(12) United States Patent
Fuller et al.

(10) Patent No.: US 9,078,612 B2
(45) Date of Patent: Jul. 14, 2015

(54) DEVICES AND METHODS FOR NONINVASIVE MEASUREMENT OF INTRACRANIAL PRESSURE

(75) Inventors: Terry A. Fuller, Rydal, PA (US); Yongping Wang, Philadelphia, PA (US); Anthony Bellezza, Cherry Hill, NJ (US); William Lai, Philadelphia, PA (US)

(73) Assignee: Third Eye Diagnostics, Inc., Bethlehem, PA (US)

( * ) Notice: Subject to any disclaimer, the term of this patent is extended or adjusted under 35 U.S.C. 154(b) by 762 days.

(21) Appl. No.: 13/309,920

(22) Filed: Dec. 2, 2011
(Under 37 CFR 1.47)

(65) Prior Publication Data

US 2013/0144185 A1 Jun. 6, 2013

(51) Int. Cl.
*A61B 3/16* (2006.01)
*A61B 5/03* (2006.01)

(52) U.S. Cl.
CPC .. *A61B 3/16* (2013.01); *A61B 5/031* (2013.01)

(58) Field of Classification Search
CPC ........ A61B 5/031; A61B 5/6821; A61B 3/12; A61B 3/1208; A61B 3/1233; A61B 3/1241; A61B 3/14; A61B 3/16
USPC ................................................. 600/398, 561
See application file for complete search history.

(56) References Cited

U.S. PATENT DOCUMENTS

| | | | |
|---|---|---|---|
| 3,446,061 A | 5/1969 | Draeger et al. | |
| 3,706,304 A * | 12/1972 | Sisler | 600/489 |
| 3,832,891 A | 9/1974 | Stuckey | |
| 3,977,237 A | 8/1976 | Tesi | |
| 4,523,597 A | 6/1985 | Sawa et al. | |
| 5,070,875 A | 12/1991 | Falck et al. | |
| 5,355,884 A | 10/1994 | Bennett | |
| 6,083,160 A | 7/2000 | Lipman | |
| 6,093,147 A | 7/2000 | Kontiola | |
| 6,129,682 A * | 10/2000 | Borchert et al. | 600/561 |
| 6,179,779 B1 | 1/2001 | Falck et al. | |
| 6,413,214 B1 | 7/2002 | Yang | |
| 6,471,647 B2 | 10/2002 | Falck et al. | |
| 6,736,778 B2 | 5/2004 | Falck, Jr. et al. | |
| 6,776,756 B2 | 8/2004 | Feldon et al. | |
| 7,122,007 B2 | 10/2006 | Querfurth | |
| 7,153,267 B2 | 12/2006 | Falck, Jr. et al. | |
| 2002/0049389 A1 * | 4/2002 | Abreu | 600/558 |

(Continued)

OTHER PUBLICATIONS

Echegaray, Sebastian, et al. "Automated analysis of optic nerve images for detection and staging of papilledema." Sep. 2011. Investigative Opthamology & Visual Science, vol. 52, No. 10. pp. 7470-7478.*

(Continued)

*Primary Examiner* — Adam Eiseman
(74) *Attorney, Agent, or Firm* — Baker & Hostetler LLP

(57) ABSTRACT

Provided are systems and methods for noninvasively assessing intracranial pressure by controllably applanating at least a portion of a subject's ocular globe so as to collapse an intraocular blood vessel and correlating the collapse pressure to intracranial pressure. Also provided are ophthalmic components useful in ophthalmic imaging applications, as well as methods of assessing intracranial pressure that are based, at least in part, on the degree of papilledema, if any, present in the subject.

12 Claims, 12 Drawing Sheets

(56) References Cited

U.S. PATENT DOCUMENTS

| | | | |
|---|---|---|---|
| 2004/0230124 A1* | 11/2004 | Querfurth | 600/485 |
| 2005/0020896 A1 | 1/2005 | Fuller et al. | |
| 2006/0206037 A1* | 9/2006 | Braxton | 600/561 |
| 2006/0217611 A1 | 9/2006 | Falck, Jr. et al. | |
| 2006/0235313 A1 | 10/2006 | Falck, Jr. et al. | |
| 2007/0123769 A1 | 5/2007 | Fuller et al. | |
| 2007/0173713 A1 | 7/2007 | Falck, Jr. et al. | |
| 2008/0077000 A1 | 3/2008 | Falck, Jr. et al. | |

OTHER PUBLICATIONS

Querfurth et al, "Prediction of Intracranial Pressure From Noninvasive Transocular Venous and Arterial Hemodynamic Measurements", Neurocritical Care, 2004, 1(2),183-194.

Querfurth et al, "Ophthalmodynamometry for ICP Prediction and Pilot Test on Mt. Everest" BMC Neurology, Nov. 2010, 10:106.

Kimberly et al., "Correlation of Optic Nerve Sheath Diameter with Direct Measurement of Intracranial Pressure", Society for Academic Emergency Medicine, 2008, 15(2), 201-204.

* cited by examiner

Section A-A'

DEVICES AND METHODS FOR NONINVASIVE MEASUREMENT OF INTRACRANIAL PRESSURE

TECHNICAL FIELD

The present disclosure relates to the field of neurological instrumentation and more specifically to the field of measuring intracranial pressure.

BACKGROUND

Intracranial pressure (ICP) is measured for the diagnosis and the management of disorders such as hydrocephalus and pseudotumor cerebri. ICP is often measured following serious head injury, stroke edema, and intracranial hemorrhage, and is also of value in the management of certain neurological or ophthalmic diseases that are associated with increased cerebral pressure.

The current standard of care to measure ICP involves surgically inserting a sensor into the cranium through an access hole drilled through the skull. Present treatment techniques for monitoring ICP or managing intracranial hypertension (ICH) generally require invasive placement of subarachnoid bolts, counter-pressure epidural devices (Ladd or Camino fiber-optic monitors) or intra-ventricular catheters coupled to external pressure monitors. Such surgical procedures carry the risk of complications including infections, hemorrhage, herniation, damage to nervous tissue, and death, and are very expensive. In addition, cerebrospinal fluid pressure may be altered the instant the measurement is performed as a result of leakage of cerebrospinal fluid. Despite the risks, invasive measurements of ICP are nonetheless commonplace, as they provide a treatment option in addition to a diagnostic option, which non-invasive devices cannot.

Because of these risks, ICP is only measured in patients who are critically ill and is not a practical solution for assessing the severity of a patient's injury or in triage. Accordingly, there is a need for non-invasive, momentary assessment of ICP in certain acute situations such as patients with acute shunt obstruction, in the neuro-intensive care unit (NICU) when lumbar puncture is not practical, in the emergency room or by emergency medical technicians (EMT) and other civilian and military first-responders in response to head injury or the like.

Existing attempts to accurately and non-invasively determine ICP are not optimal, as such approaches do not provide a reliable measure of ICP. Individual baseline variability due in part to anatomical variances further limits the application of these methods. Additionally, these methods have demonstrated insufficient precision when compared to invasive ICP monitors. Accordingly, there is an unmet need in the art for easy to use, portable and inexpensive devices and methods capable of non-invasive determination of intracranial pressure.

In addition to the patient conditions summarized above in which an assessment of ICP is desirable, the field would also benefit from devices and methods capable of providing a more accurate diagnosis of glaucoma. Traditionally, a patient's intraocular pressure (IOP) has been to the single most important metric that determines a patient's susceptibility to glaucoma. Knowledge of a patient's ICP in addition to a patient's IOP will provide the clinician with the translaminar pressure (i.e., the pressure difference between IOP and ICP that is applied to the optic nerve head), which may be a more accurate indicator of glaucoma susceptibility than IOP alone.

SUMMARY

In a first aspect, the present disclosure provides methods of estimating intracranial pressure in a subject, comprising imaging an intraocular blood vessel while applying a force so as to at least partially applanate (i.e., flatten) a portion of the ocular globe and increase intraocular pressure to a level sufficient to collapse an intraocular blood vessel; estimating, by one of several methods of determining intraocular pressure, the intraocular pressure that collapses the intraocular blood vessel; and correlating the estimated intraocular pressure that collapses the intraocular blood vessel to an estimated intracranial pressure of the subject. Exemplary methods of determining intraocular pressure include, e.g., corneal applanation tonometry, pneumotonometry, electronic indentation tonometry, transpalpebral tonometry, and the like.

In another aspect, the present disclosure provides systems for measuring intracranial pressure configured to controllably at least partially applanate at least a portion of the ocular globe of a subject's eye, measuring intraocular pressure and suitably collecting images from retinal blood vessels. In one illustrative embodiment, retinal blood vessel images are concurrently collected with a means of determining intraocular pressure from the measured force on the globe and determination of the area of flattening or depression of the ocular globe.

The present disclosure further provides ophthalmic components that may be referred herein as applanation caps. These components suitably include a body having an optical surface adapted to contact a subject's cornea, the body being adapted to engage with an applanating instrument, and the component comprising a lens, a prism, or both. In some embodiments, the lens or prism is formed in the body. In others, the lens or prism is bonded to the body. The applanation cap may contain one or more indicia to assist the ICP measurement system to know its type or function. Further, the indicia may alter or control system electronics to modulate system operation and data collection. The ophthalmic component may, in some embodiments, include a refractive surface approximating that of an unapplanated cornea. The lens, prism, or both, may be formed on one surface of the ophthalmic component.

The present disclosure further provides systems for imaging the retinal fundus concurrently collected with a means of determining intraocular pressure for the purposes of determining intracranial pressure in the presence of papilledema or grading papilledema.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale or proportion. In the drawings.

DETAILED DESCRIPTION OF ILLUSTRATIVE EMBODIMENTS

Figure 1:
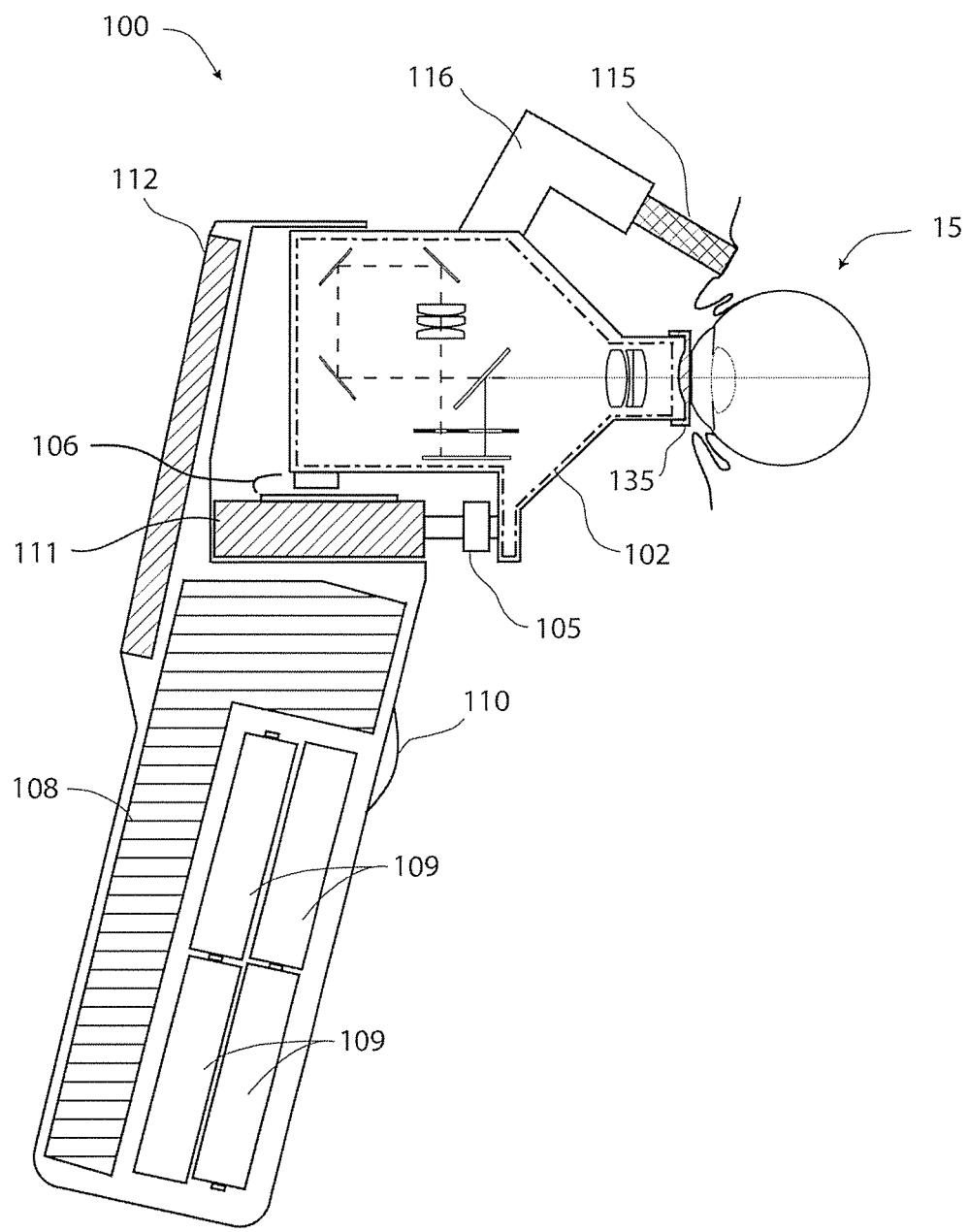
FIG. 1 depicts an exemplary intracranial pressure measuring system according to the present disclosure.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "approximately" or "about," it will be understood that the particular value forms another embodiment. All ranges are inclusive and combinable, and all publications cited herein are incorporated by reference in their entireties for any and all purposes.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

To fully describe the application of the disclosed methods and systems to ICP measurement and to describe why pressure in retinal vessels is well-correlated to ICP, a review of the anatomy and physiology of the eye and surrounding tissues is useful. The optic nerve connects the retinal ganglion cell axons within the eye to the brain and is completely surrounded by the subarachnoid space. The subarachnoid space is filled with cerebrospinal fluid (CSF), and the pressure of this fluid is equivalent to ICP. The central retinal artery, vein and central retinal nerve travel through the central region of the optic nerve, converging at the optic nerve head in the back of the eye. As CSF pressure increases, the pressure in the subarachnoid space increases, which exerts an increasing pressure on the optic nerve. This increased fluid pressure in turn applies a pressure around the central retinal vessels that travel within the optic nerve, causing an increase in blood pressure in the central retinal vessels proportional to the CSF constriction pressure.

In one aspect, the present disclosure provides methods of estimating intracranial pressure in a subject. These methods include, inter alia, imaging an intraocular blood vessel while applying a force to a subject's ocular globe so as to at least partially applanate at least a portion of the ocular globe and increase intraocular pressure so as to collapse an intraocular blood vessel. The force may be applied directly to the subject's cornea or sclera, but this is not a requirement, as force may be applied to an eyelid (upper or lower) of the subject so as to indirectly applanate a portion of the ocular globe.

The methods also include estimating, suitably by controllably imaging the applanated portion of the subject's ocular globe, the intraocular pressure that collapses the intraocular blood vessel; and correlating the estimated intraocular pressure that collapses the intraocular blood vessel to an estimated intracranial pressure of the subject. This may be performed in an automated fashion, and embodiments where a computer controller and processor act to controllably apply the applanating force and collect images of the applanated portion of the eye and of the blood vessel are considered especially suitable. Embodiments where a computer processor correlates the applanated area of the ocular globe to the applied pressure that collapses the blood vessel are considered suitable.

The at least partially applanated portion of the subject's ocular globe suitably includes a portion of the sclera, a portion of the cornea, or even both. This may be affected by a manually-controlled device or by an automated or computer-controlled device. The user may suitably applanate the ocular globe by pressing directly on the ocular globe. Alternatively, the user may press on an eyelid of the subject so as to applanate the ocular globe. The applantation may be effected by a flat-end rod or other shaped device. Ultrasound probes may be used as applanators, as an ultrasound probe may be used to apply force to the eye, and even to image the blood vessel of the eye, in some cases. In some embodiments, the ultrasound probe may be contacted to the eyelid or the cornea of the subject so as to applanate the ocular globe, with the ultrasound probe also being used to image the blood vessel in the eye.

In some embodiments, the methods suitably include estimating the intraocular pressure that collapses the intraocular blood vessel by correlating one or more images of the applanated portion of the subject's ocular globe to the applied force corresponding to the one or more images of the applanated portion of the subject's ocular globe. The user may image the applanated portion of the subject's ocular globe while applying a first, reference applanating force. Subsequent to or continuous with application of this first reference force, a known increasing force is continuously applied while images of the applanated area are simultaneously obtained.

Concurrent with obtaining images of the applanated area, the user may obtain images of the retina in which the central retinal vessels can be observed. These retinal images may be synchronized with the applanation area images and force application data so that when a collapse of one of the central retinal vessels is observed in the retinal images, the applanation area and applied force at that moment in time is known.

Knowledge of the applanation area and applied force at that moment allows the user to calculate the intraocular pressure at the time of vessel collapse, and therefore estimate the pressure within the vessel at the time of collapse. Alternatively, applanation area images and force application data from moments immediately before and/or immediately after the moment of observed retinal vessel collapse may be used to calculate intraocular pressure at the moment of vessel collapse. Other means of measuring intraocular pressure at the moment of collapse can also be utilized in accordance with the invention. For example, applanating the ocular globe and viewing the retinal vessels, synchronized with transpalpebral or pneumatonometric estimates of intraocular pressure may be used.

Figure 2:
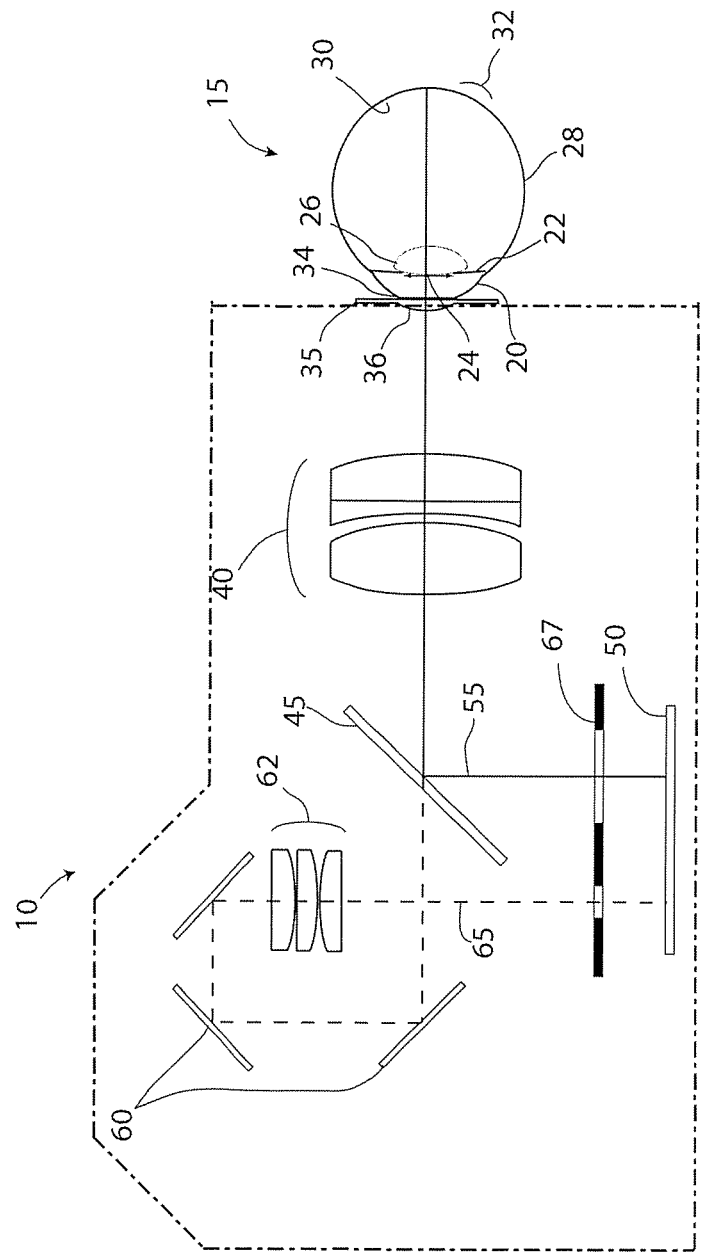
FIG. 2 depicts an exemplary single image sensor optical imaging system according to the present disclosure.

Imaging may, as described herein, be effected by one or more image collectors. As shown in FIG. 2, for example, a user may collect images of the ocular globe and of the collapsed or collapsing blood vessel on a single image detector. Alternatively, a user may employ one image detector to collect an image of the ocular globe and another image collector to collect images of the blood vessel or vessels of interest, as illustrated in FIG. 5.

Figure 5:
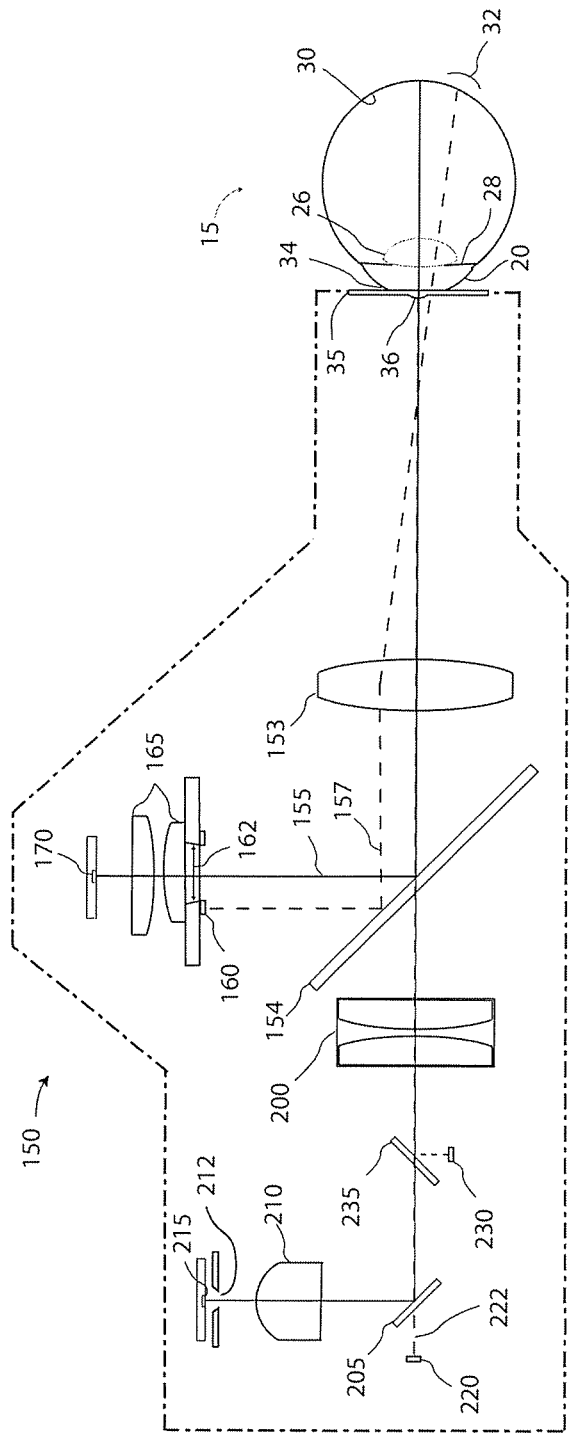
FIG. 5 depicts a first exemplary dual image sensor system according to the present invention.

Applanating the globe to elevate and measure intraocular pressure and to view retinal vessels to determine the point of retinal vessel collapse is one central element that may be accomplished, for example, by sharing optical elements, an imaging axis and imaging sensors as shown in FIGS. 1 and 2 or accomplished using separate optical elements, imaging axes and imaging sensors as shown in FIG. 5 for example. It is understood that imaging of the retina may be accomplished in a variety of optical configurations understood in the art. In the present invention and using such configurations, accommodation may be made to permit concurrent applanation of the ocular globe and determination of intraocular pressure through applanation area and force.

Illustrative FIG. 1 shows an optically clear applanation cap at the distal end of a device used to applanate the cornea, which cap also provides an optical pathway through which the retinal images can be obtained. In this embodiment, the central anterior portion of the cap has a convex-plano shape to enhance retinal imaging. It should be understood that an applanation cap may have a plano, convex, concave, a prism, or any combination of surfaces thereof. For example, a cap may be plano-plano in configuration. Alternatively, a cap may be a prism-plano. A cap may also be convex-concave. The convex surface or lens compensates for some or all of the refractive power of the cornea lost when the cornea is flattened or applanated. The cap may have a plano-plano configuration or may contain other prismatic corrections to image the off-axis optic disk, as convex-plano caps are not a requirement. The retinal vessels observed in the retinal images may be illuminated by ambient light or by a provided illumination system. The retinal illumination system can comprise an illumination source that is co-axial with the optical path and converge at an apex. Alternatively, in one embodiment the illumination source can comprise multiple off-axis illumination paths.

Estimation of the intraocular pressure at which a central retinal vessel will collapse may be performed by analyzing synchronized retinal images, applanation surface images and force application data. This estimation may be performed during or after the ocular globe has been applanated. In such an estimation the user may review or inspect the retinal blood vessel images, the synchronized applanation surface images and the force applied to the globe to determine the intraocular pressure at the moment of collapse of the intraocular blood vessel. A function can be derived based on using the resting IOP as an initial condition and the calculating the amount of fluid displaced from the anterior chamber as the cornea is applanated. For example, for an eye with a resting IOP of 10 mmHg (millimeters mercury), a 9.8 gram-force to applanate an area of 38 square millimeters would result in an IOP estimate of 18 mmHg. With a resting IOP of 15 mmHg, a 12 gram-force to applanate an area of 34 square millimeters would result in an IOP estimate of 25 mmHg. One exemplary method of estimating IOP (e.g., for applanated areas greater than 3.06 mm in diameter is set forth by Eisenlohr et al., *Brit J. Ophthal.* (1962) 46, 536).

In some embodiments of the present invention, the methods include automated or semi-automated determination of the pressure that collapses the intraocular blood vessel. In such embodiments, the user may employ an automated image processing that compares sequential images of the intraocular blood vessels to determine the moment in time when collapse of the central retinal blood vessel occurs, and therefore through the synchronized data the applanating force at that moment in time. One or more of the optical density, color, and caliber of the vessels will change upon vessel collapse, and these characteristics are suitable for automated or manual determination.

Imaging the intraocular blood vessel is suitably accomplished by collecting an image of the retinal fundus on an image collector. Suitable image collectors include focal plane arrays, such as CCD devices, CMOS devices, and the like. The focal plane array may be a two-dimensional array such as those available from Aptina (San Jose, Calif.), or Cypress Semiconductor Corporation (San Jose, Calif.), or even be a linear array such as those available from Goodrich Corporation (Princeton, N.J.).

The periocular arteries that supply blood to tissues and structures of the eye pass through the cerebral spinal fluid (CSF) and are sensitive to changes in CSF pressure. Systolic and diastolic blood flow velocities are subject to a complex auto-regulatory process in which the periocular arteries continue to supply sufficient blood circulation to the eye even when a patient has an elevated ICP. As pressure increases surrounding the blood circulation to the eye, various blood flow parameters in the central retinal and ophthalmic arteries are also affected.

The user may, in some embodiments, obtain Doppler ultrasound information from a periocular blood vessel of the subject to improve the accuracy of correlation between the present invention and invasive measurements of ICP. Periocular blood vessels within the cranium are located within or close to the eye. Examples include the ophthalmic artery, the central retinal artery and vein, superior and inferior ophthalmic veins, the middle cerebral artery, etc. Locating a periocular blood vessel is suitably performed by insonating the vessels that supply the globe and exit the cranium through the optic canal or cavernous sinus. Auditory and/or visual signals without imaging may also be used to indicate that a vessel has been identified. An example of an auditory signal may include changes in sound pitch in response to changes in blood flow. An example of a non-imaging visual signal may include a linear LED array that lights successive LED's in response to increased sensed blood flow.

A variety of blood flow parameters may be used in estimating ICP (see, e.g., U.S. Pat. No. 7,122,007 to Querfurth, incorporated herein by reference in its entirety). Pulsatility index ("PI"), resistivity index ("RI"), systolic velocity, diastolic velocity, and the like are all suitable velocity indicia for use in the system. PI is considered a particularly suitable velocity parameter for use in the system. Blood velocity in vessels within the cranium is affected by intracranial pressure. Blood velocity, particularly in the arteries, is not constant for a given intracranial pressure, but varies in relation to the status of the cardiac cycle. Maximum blood velocity is termed "peak systolic blood velocity", and corresponds to maximum heart contraction. Minimum blood velocity occurs during the time that the heart is filling with blood (diastole) and is termed "end diastolic blood velocity."

$$PI = \frac{\text{(Peak systolic velocity} - \text{End diastolic velocity)}}{\text{Mean velocity}}$$

$$RI = \frac{\text{(Peak systolic velocity} - \text{End diastolic velocity)}}{\text{Peak systolic velocity}}$$

As pressure increases surrounding the blood circulation to the eye, the resistivity and pulsatility of the blood flow in the central retinal and ophthalmic arteries are also affected.

It has been determined that intracranial pressure can be accurately estimated as a function of ophthalmic parameters including central retinal venous pressure (CRVP) and arterial blood velocity (ABV), where ABV may be assessed using PI, RI, or another blood velocity metric:

ICP=*f*(CRVP,ABV)

Using sequential measurements from multiple devices one may fit data to the form ICP=A+Bx. Following the methods and systems described herein, one such functional relationship may be expressed in the form ICP=A+Bx+Cy, where x is central retinal vein pressure (CRVP) and y is the pulsatility index (PI) of the ophthalmic artery. A, B and C are scalars used to fit clinical data and depend on the manner of which the ophthalmic parameters are collected. For instance, A and B can be adjusted based on the method of tonometry (pneumotonometry, transpalpebral, or applanation) and C can be adjusted based on the periocular vessel chosen for the measurement. By way of example and based on clinical experience following the methods and systems described, one may correlate the CRVP plus the Doppler ultrasound pulsatility index of the ophthalmic artery to ICP using the following regression equation:

$$ICP = 0.294 + 0.735(CRVP) + 0.735\left(\frac{1}{PI}\right).$$

ICP functions like the one above may be further improved in accuracy by including additional independent variables. The embodiments described herein focus on ophthalmic parameters not previously considered in a unified expression; biomechanical variables including but not limited to optic disc swelling or other ocular biomechanical properties that are affected by elevated ICP. These peripapillary ophthalmic parameters can be incorporated into an independent ophthalmic tissue variable (OT), in units of stress. Thus:

ICP=*f*(CRVP,ABV,OT).

In addition, patients in need of a determination of intracranial pressure may, in some cases, also have papilledema, a swelling of the optic disc that occurs secondary to elevated intracranial pressure. Papilledema develops in a stepwise fashion, and can be tracked by medical professionals using a widely accepted grading scheme first proposed by Frisén (Stavern 2007 "Optic Disc Edema" in Seminars in Neurology, vol. 27, no. 3, pages 233-243, 2007); and S. Echegaray, "Automated Analysis of Optic Nerve Images for Detection and Staging of Papilledema" (in Investigative Ophthalmology and Visual Science, vol. 52, no. 10, pages 7470-7478, 2011). The Modified Frisén Scale classifies papilledema into six grades from 0 (normal) to 5 (severe). Each grade is characterized by a set of objective, visual features observed on the optic disc and peripapillary retina. A device that captures images of the optic disc and surrounding peripapillary retina and classifies papilledema using the Frisén grading method will not only provide the ability to objectively assess papilledema severity, but will be able to use the level of papilledema severity as an input to an algorithm for more accurately determining ICP.

Another method of assessing papilledema severity in order to more accurately determine ICP is to use ocular coherence tomography (OCT) to measure peripapillary retinal nerve fiber layer (RNFL) thickness. Swelling of the peripapillary retina due to elevation in ICP will cause an increase in the RNFL thickness. Therefore, a technique that can provide RNFL thickness can be used to improve an algorithm for determining ICP.

For example, one such variable, the severity of papilledema present in some patients with elevated ICP, may be used to modify the above equation. Papilledema and its associated swelling of the tissues of the optic disc and surrounding retina due to an increase in axoplasmic fluid surrounding the axons, may cause an increase in bulk tissue pressure ($P_{BT}$). This bulk tissue pressure will contribute (along with the cerebrospinal fluid pressure, or ICP) to the overall pressure being applied to the central retinal vein. The magnitude of $P_{BT}$ is correlated with the severity of papilledema, and may therefore correlate with the papilledema grade from the modified Frisén scale (MFS). In this case OT is a function of $P_{BT}$ or, OT=f($P_{BT}$). One may use MFS to obtain OT or, OT=f(MFS).

Another method of assessing papilledema (and therefore assessing $P_{BT}$) is to use OCT to measure peripapillary RNFL thickness. OCT is a non-invasive technique that provides cross-sectional images of the RNFL and provides absolute measurements of the fiber layer thickness. Increases in the thickness of this fiber layer are directly correlated to the severity of papilledema, and so OT=f(RNFL). Incorporating the OT component into the ICP functional equation above yields:

$$ICP = A + B(CRVP) + C\left(\frac{1}{PI}\right) - D(OT),$$

where A is directly proportional to the Frisén Scale papilledema grade. As set forth above, a user may estimate intracranial pressure by basing that estimate at least in part on an assessment of the degree, of any, of papilledema that may be present in the subject. The papilledema assessment is suitably based on the Frisén or modified Frisén scale. The assessment may be performed in an automated fashion. One such approach to an automated assessment of papilledema presence is set forth by S. Echegarry et al. Alternatively, the assessment of papilledema may be made by way of optical coherent tomography (OCT), as described herein.

Accordingly, as set forth above, the present disclosure provides methods of assessing the intracranial pressure of a subject. These methods include, inter alia, estimating intracranial pressure by combining an assessment of the level of papilledema, if any, present in the subject with one or more of a blood velocity of the subject, a blood vessel pressure of the subject, a tissue thickness of the subject, or any combination thereof. The tissue thickness may, for example, be the thickness of the retinal nerve fiber layer, the thickness of the prelaminar optic nerve head tissue, or some combination of these. The blood velocity may be a systolic velocity, a diastolic velocity, or any combination thereof, such as the PI and RI indices described herein. The papilledema level comprises a Frisén scale score of the papilledema. The assessment of the papilledema level, the tissue thickness, or both, is based on optical coherent tomography (OCT) or other methods to measure peripapillary RNFL thickness, prelaminar optic nerve head tissue thickness, or other ocular tissues.

The present disclosure also provides systems for measuring intracranial pressure in a subject. These systems suitably include a portion (the "applanator") to controllably at least partially applanate (i.e., at least partially flatten) at least a portion of the ocular globe of a subject's eye. This applanation may be effected by contacting to the eye an applanation portion or even by an ophthalmic component, which may also be referred to as an applanation cap. It should be understood that the applanation may be effected by applying a force to, e.g., the eyelid of the subject, the cornea or sclera of the subject, or two or more of the foregoing.

The systems suitably include at least a first image collector configured to collect light from an intraocular blood vessel of the subject's eye, and a retinal illumination train that may be configured to direct light through an ophthalmic component (which may be referred to as an applanation cap) to the intraocular blood vessel of the subject's eye and to direct light reflected from the intraocular blood vessel to the image collector and a microprocessor. An image collector may be configured to view the intraocular blood vessel in the absence of a system illumination train. For example, a sensitive, low-light image sensor may be used to collect images illuminated by ambient light. Alternatively, an infrared sensitive image sensor may also be used. The applanation cap (as one illustrative ophthalmic component) may be sterile and removably affixed or otherwise engage with an applanator. The applanator may be a motor-controlled optical module as describe below, but may also be manually controlled and advanced.

The system of the present disclosure can be configured using one or more focal plane array image sensors for imaging the retina and the applanated portion of the globe of the subject. In one embodiment a single image sensor is configured to collect images from both the retina and the interface between the cornea and an applanation cap (which may be referred to as "corneal imaging" or "corneal image"). The images can be collected simultaneously or in rapid and repeating succession. A single image sensor system may be configured into a light weight, compact system. In a single sensor system the image sensor may be required to continuously collect high-speed images for applanation analysis and high-resolution images of retinal vessel analysis. Alternatively, rapid sequential image collection may be utilized that require the single sensor to sequentially change from high-speed low-resolution to low-speed high-resolution data collection. Presently, sensors operating in either configuration are suitable but relatively expensive.

In another embodiment, two separate arrays may be utilized for retinal and corneal image capture to overcome the limitations of a single sensor system. A system has been effectively constructed using a first sensor to collect images from the retina and a second sensor to collect images from the applanated portion of the globe.

The motion of the applanator may be manually-controlled. Alternatively, the applanator may be computer-controlled. Any suitable method of advancing the applanator can be used. Electromagnetically driven mechanisms, e.g. a voice coil motor, were successfully clinically tested. However, other motion control mechanisms such as conventional and stepper motors, pneumatic actuators and the like may also be utilized. Electromagnetically driven mechanisms, including voice coil motors, have added advantages. In addition to inducing controllable displacement of the applanator, they also produce an electrical indication of the force being exerted.

The applanation cap may be of any material compatible with the cornea such as polycarbonate, polymethyl methacrylate (PMMA) or even glass. Transparent materials are especially suitable for applanation caps and ophthalmic components. The applanation cap diameter can range from about under 4 mm to over 15 mm. One parameter that may at least partially determine the applanation cap size is the degree to which the globe is applanated. For an adult cornea, a convenient size is 10 mm. The applanation cap may suitably be transparent, although transparency is not a requirement. The applanation cap may be translucent or opaque as well, which may be suitable for use when the applanation portion (e.g., ophthalmic component or applanation cap) contacts the eyelid or sclera. In some embodiments, the applanation portion includes a lens, prism, or both formed in a plano body.

The applanation cap may have an engagement portion configured to engage with an optical module suitably movable for contact with the ocular globe. The applanation cap is suitably constructed to be sterile and removably affixed to the optical module and able to snap on, screw onto, be magnetically held or otherwise affixed thereto. The cap may be reusable or disposable.

The applanation cap may bear one or more indicia. These indicia (which may be present in the form of letters, numbers, barcodes, or even electronic form) may be used to identify the applanation cap in terms of clinical use, size, shape, or other characteristic. For example, a particular index may convey that the applanation cap bearing the index is sized for use in pediatric patients. Since a child's globe is far smaller than an adult's, use of an appropriate applanation cap may eliminate the need for focus adjustments and associated mechanical and optical complexity. Further, it can notify system electronics of the requisite operating parameters (maximum force, etc.) that can be exerted on the child's eye.

The disclosed methods and systems may be used for indications other than traumatic head injury. For example, when measuring resting intraocular pressure in patients with glaucoma or ocular hypertension, one would not require an applanation cap incorporating retinal imaging compensation optics. The indicia will notify the system parameters of the device's intended use and settings and, in this case, appropriately limit the applanation force. In this manner, a system may include a set of one or more applanation caps so as to accommodate subjects that are themselves different. For example, an emergency medical team might maintain a set or kit of multiple caps so as to accommodate patients of various sizes. The systems and methods may also be configured obtain a translaminar pressure (i.e., the pressure difference between IOP and ICP that is applied to the optic nerve head), which may be used as a more accurate indicator of glaucoma susceptibility than IOP alone.

In some embodiments, the ophthalmic component is configured so as to direct light reflected from the intraocular blood vessel to the first image collector. The ophthalmic component may also be configured to direct an image of an interface between the ophthalmic component and an applanated region of the ocular globe to the first image collector. The system may be configured to direct an image of the collapsing or collapsed blood vessel and an image of the component-ocular globe interface to a single image collector, as illustrated in FIG. 2. In other embodiments, the images are directed to separate image collectors, as illustrated in FIG. 5

In some embodiments, the system is capable of self-configuring in response to indicia on the applanation cap. For example, the system may adjust the applanator, the image collector, or even the illumination train in response to one or more indicia present on the applanation cap. As one example, an auto-focus motor could pre-adjust the location of the imaging sensor prior to the beginning of data collection, corresponding to the patient's eye size (as indicated by the choice of applanation cap).

The system may be configured such that during operation it concurrently applies a force to the subject's globe and collects, from an image collector, images from at least one of an intraocular blood vessel of a subject's eye and an interface between the applanating portion and the ocular globe of the subject's eye. Applanation of the cornea and simultaneous visualization of the retina has been found to be a particularly convenient configuration. In this configuration, applanation does not cause lateral movement of the ocular globe or distort the view of retinal vessels. In addition, all measurements are made along the same axis. In certain embodiments, the system is configured to, during operation, concurrently applanate at least a portion of the subject's ocular globe and collect, on the first image collector, light reflected from the intraocular blood vessel of the subject's eye.

An illumination train may, in some embodiments, include one or more light sources such as a light-emitting diode (LED), an incandescent lamp, an electroluminescent light source, and the like. In some embodiments and as most clearly shown in FIG. 6 in conjunction with FIGS. 7 and 8, the illumination train includes light-emitting diodes arranged in a circular or ring configuration. It should be understood that light emitted from the light sources may have a wavelength in the visible light range (wavelength approximately 400 nm to 700 nm), but may also be infrared light (wavelength approximately 700 nm to over 1,200 nm). Thus, the term "light" as used herein shall be understood to mean energy in the visible and near infrared regions of the electromagnetic spectrum.

Systems may also include a fixation illuminator configured so as to provide a reference point for the subject to align the ocular globe. Such illuminators may be a light source upon which the subject focuses while the system is operating on the subject. In this way, the subject's eye is stabilized and maintains a consistent orientation during operation of the device.

Systems may further include a Doppler instrument configured so as to collect ultrasound data from a periocular blood vessel of the subject. Examples of periocular blood vessels include the ophthalmic artery, the central retinal artery and vein, the lacrimal artery, posterior ciliary arteries, superior and inferior ophthalmic veins, and middle cerebral artery. Ophthalmic artery insonation requires penetration of approximately 40 to 50 mm. For this amount of tissue penetration, an ultrasound probe of between 7 MHz and 10 MHz is preferred. Locating a periocular blood vessel is suitably performed by using a color Doppler ultrasound imaging system. Examples of such devices are commercially available from General Electric (www.ge.com) and Philips (www.philips.com). Alternatively, a non-imaging Doppler ultrasound system with auditory and/or visual feedback signals locate a periocular blood vessel by scanning the anatomical volume of interest using a linear probe can be used. One such device is an ultrasound transducer manufactured by Multigon Industries. The Doppler sensor may be adjustably fixed to the body of the invention as shown in FIG. 1 or may be separately held.

The systems may, in some embodiments, be configured so as to be capable of assessing the degree, if any, of papilledema present in the subject. In one illustrative embodiment, the system is configured to obtain one or more images of the fundus of the subject and compare at least one of these images to a library image of a fundus, and generate a papilledema grade for the subject. The system may include a processor configured to estimate intracranial pressure of the subject based on one or more images of the at least partially applanated potion of the subject's eye and one or more images of the intraocular blood vessel of the subject's eye. The papilledema assessment method of S. Echegaray et al., is considered especially suitable for application to the disclosed systems and methods.

The systems in the present disclosure may include an applanator configured to controllably contact an applanation portion (which may also be referred to as an ophthalmic component or an applanation cap) to the ocular globe of a subject's eye. Suitable applanators are described elsewhere herein. The systems may also include an image collector configured to collect light reflected from an intraocular blood vessel of the subject's eye. The system may also include an illumination train configured to direct light through the applanation portion to the intraocular blood vessel of the subject's eye and to direct light reflected from the intraocular blood vessel to the image collector. During operation, the system may record retinal fundus images and score features of the optic disc using image processing algorithms known to those of skill in the art. The system may be configured to compare feature scores to a database of images for the purpose of grading papilledema according the Modified Frisén scale. The system may be configured to output a Frisén scale score of papilledema paired with an image of the optic disc for purposes of tracking papilledema progression. The system may thus assess a subject's papilledema and assess the patient's condition over time. In some configurations, the system generates a papilledema score in an automated fashion. The systems may be configured to, during operation, record retinal fundus images, score features of the optic disc using image processing algorithms, or both. The systems may also be configured to compare feature scores to a database of images for so as to grade the purpose of grading papilldema, if present, according the Modified Frisén Scale.

Further disclosure is now made by reference to the attached figures.

FIG. 1 illustrates a cutaway view of an exemplary intracranial pressure measuring system according to the present disclosure. As shown, ICP measuring system 100 suitably includes a movable optical module 102 that engages with applanation cap 135. A motion control module 104 (not shown) may modulate the motion of the applanator. Electronics module 108 contains units adapted to control and modulate the device's actions and operations. Optical module 102 collects retinal images simultaneously with electronic module 108 collecting force and position data from force sensor 105 and position sensor 106, respectively. Motion of optical module 102 to applanate a portion of ocular globe 15 may be manual or automatic. Automatic motion of the optical module is suitably controlled by motor 111, force transducer 105 and position sensor 106. Optical module 102 suitably translates in a range of several centimeters, e.g., by 0.5, 1, 2, 3, 4, or even 5. During operation and upon contact with the cornea, force transducer 105 limits the force to appropriately safe levels of intraocular pressure and the portion of ocular globe 15 applanated. Position sensor 106 may limit translation to under approximately 4 mm (subject to the size of the subject's eye) so as not to harm the subject. Following data collection, which nominally takes approximately 5 to 10 seconds, optical module 102 automatically retracts. If desired by the user, a scroll wheel, lever, slide or the like may be used to review the applanation force and the images of the retina on display 112 collected during actuation so as to identify the instant of vessel collapse. The identification of the instant of vessel collapse may also be automatic.

Figure 12:
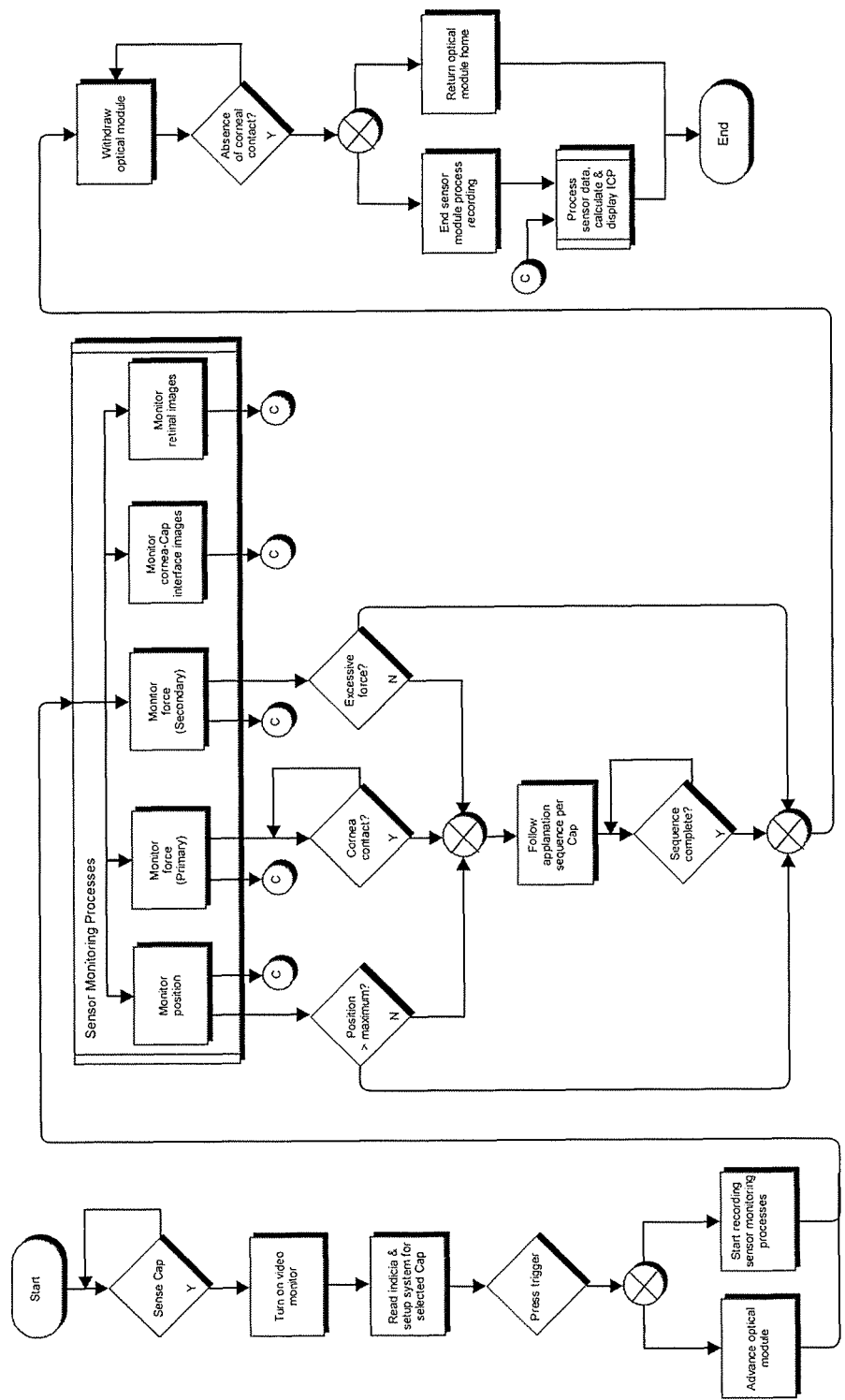
FIG. 12 depicts an exemplary flow diagram of the operation of an intracranial pressure measuring system.

The sensor used to determine force applied to the globe may be any form of force transducer, including one or more of electrical resistance, foil, semiconductor or thin film strain gauges and other force measurement devices. Force transducer 105 can be located in any position in ICP measuring system 100 that will provide a signal proportional to the force applied to the ocular globe. As shown, force transducer 105 is positioned between motor 111 and the movable optical module 102. The determination of force by sensing a change in the current from a voice coil motor drive is of particular value due to use of a single device to drive the optical module and sensitively measure the forces exerted. Locating a force sensor in close proximity to applanation cap 135 may be advantageous. Position sensor 106 provides information on the absolute position and velocity of the applanation cap. Several position sensors are readily available for this application. Hall effect sensors have been found to be suitably small, inexpensive and accurate. However, other sensors including but not limited to inductive sensors, linear variable differential transformer (LVDT) sensors, etc. may be used. ICP measurement system 100 may be equipped with a head support (not shown) so as to stabilize the position of the device on the subject. For the convenience of the operator and safety of the subject, optical module 102 and applanation cap 135 may be positioned such that applanation cap 135 will not touch the subject's globe until the system is stabilized on the subject and determined appropriate by the operator. Batteries 109 may be used to power the device. The device may also run off of household or commercial electrical lines. A trigger (not shown) may be used to actuate the device, e.g., to advance the applanator, ro take one or more images, or to effect one or more other action FIG. 12 depicts an exemplary flow diagram of the operation of an intracranial pressure measuring system. Upon powering on the apparatus ("Start"), the system senses the presence of an applanation cap and turns on the video monitor. System electronics setup the system per information provided in the selected cap's indicia. After placement of the system over the subject's eye (not shown in flow diagram), the operator depresses a trigger 110 to simultaneously advance the optical module and initiate recording of data from the five sensors. A position sensor is monitored to determine the optical modules location and velocity. A primary force sensor senses the force required to advance the cap and optical module as detect the increase in force resulting from contact with the globe. A secondary force sensor is monitored to insure that the force measured by the primary force sensor is within safe limits; else the optical module is withdrawn. A sequence of movements of the optical module is followed in accordance with the cap indicia information. Once the sequence is completed, the optical module is withdrawn from the cornea, sensor monitoring processes cease, data is analyzed and the value of ICP is displayed.

The embodiment shown in FIG. 1 also illustrates Doppler ultrasound transducer 115 suitably mounted on transducer pivot arm 116 to permit contact of Doppler transducer 115 in the periocular region and oriented towards the ophthalmic artery. A signal such as an auditory signal varies in pitch and volume that may help the operator aim the probe in the correct orientation. The Doppler device may be constantly collecting Doppler ultrasound data using either an auditory or visual feedback signal. Once transducer 115 is correctly positioned, pulsatility data may be collected and averaged over at least three heart cycles.

FIG. 2 depicts an exemplary optical configuration of a single image sensor system 10 according to the present disclosure. In such an ICP measurement system, a first image may be collected of optic disc region 32 of retina 30 and focused on a first portion of retina/cornea image sensor 50 so as to distinguish a collapsed blood vessel such as the central retinal vein. A second image may be collected indicative of the degree of applanation of the globe and focused on a second portion of retina/cornea image sensor 50. Exemplary retinal imaging path 55 is also shown, as is corneal imaging path 65.

A portion of ocular globe 15 is flattened by applanation cap 35. In the embodiment shown, the portion of globe 15 that is applanated is cornea 20. The distal surface of applanation cap 35 is shown as a flat or plano surface and proximal side is shown as a convex surface (referred to as "cap lens 36"). Light reflected from retina 30 passes through ocular lens 26, flattened cornea 20, applanation cap 35 and objective lens 40. Objective lens 40 may be comprised of one or more lenses. The light reflected from retina 30 is then reflected by dichroic beam splitter 45 onto retina/cornea image sensor 50. Light from retina 30 may be reflected from an external source of illumination (not shown). In one exemplary embodiment, retina 30 is illuminated using visible light source at 565 nm. Any number of dichroic beam splitter 45 could be utilized such as, for example purposes only, a 580 nm single-edge long-pass dichroic beam splitter that reflects >95% of wavelengths in the range of 350 nm to 570 nm and transmits 93% of wavelengths from 591 nm to >950 nm (Semrock, Inc., Rochester, N.Y.). Alternatively, light from retina 30 may be infrared energy emitted as a result of heat from retina.

Applanation of cornea 20 by applanation cap 35 causes flattening of the cornea and a resulting change in the pattern and intensity of light reflected by the cornea onto retina/cornea sensor 50. The force required to flatten cornea 20 increases with increased applanation. It is well known that by measuring the force required to applanate the cornea to a known area (typically 3.06 mm in diameter) one may estimate the intraocular pressure. So-called corneal applanation tonometry has been one standard means of measuring intraocular pressure for screening and routine management of patients with ocular hypertension and glaucoma.

In traditional applanation tonometry, corneal flattening substantially under 3.06 mm results in loss of measurement accuracy due to effects of corneal rigidity and tear-film complications. Applanation of the cornea to an area substantially greater than 3.06 mm decreases the accuracy of the measurement to greater than accepted norms of +/−0.5 mmHg. This is due to an induced increase in the patient's intraocular pressure. As a result, applanating the cornea beyond 3.06 mm is generally contraindicated, although the 3.06 mm applanation area is not a requirement or limit. In the present invention, the operator suitably elevates intraocular pressure so as to intentionally generate intraocular pressure sufficient to collapse the retinal vasculature. Estimating IOP for applanation areas greater than 3.06 mm requires modeling of the biomechanics of the cornea to determine pressure as a function of force and area. A function can be derived based on using the resting IOP as an initial condition and the calculating the amount of fluid displaced from the anterior chamber as the cornea is applanated. One exemplary method of estimating IOP (e.g., for applanated areas greater than 3.06 mm in diameter is set forth by Eisenlohr et al., Brit J. Ophthal. (1962) 46, 536).

Flattened cornea 20 can be visualized and the area of applanation determined by imaging cornea-cap interface 34 using an image sensor illuminated by any wavelength sensitive to the image sensor. However, it is preferable to select a wavelength different from that used to illuminate retina 50. In the example above using the described beam splitter and retina 50 illumination (not shown), cornea illumination source (not shown) was selected to be a 850 nm LED. It is preferable, but not a requirement, that the retina be illuminated by 540 nm to 570 nm green light. Such wavelengths provide excellent contrast and enhance visibility of the retinal vasculature. Light reflected by flattened cornea 20 passes through applanation cap 35, objective lens 40 and dichroic beam splitter 45. Bending mirrors 60 positions reflected cornea light to pass through corneal imaging lens assembly 62 and corneal portion (left) of aperture 67 and focus the corneal image on retina/cornea image sensor 50. Aperture 67 serves to reduce unwanted vignetting and backscatter of illumination from the system optics and anatomical structures such as the lens and cornea.

Figure 3:
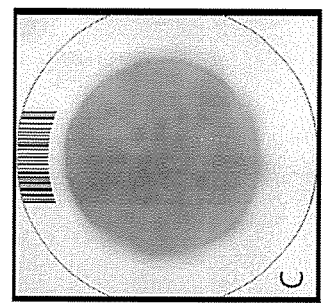
FIG. 3 depicts exemplary results of imaging an applanation surface according to the present invention.
Figure 3:
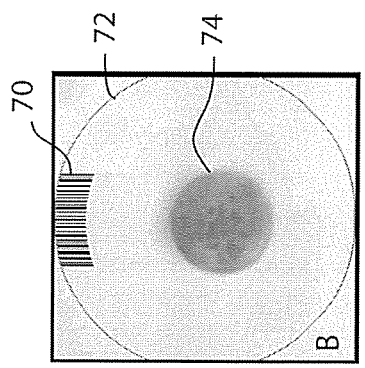
Figure 3:
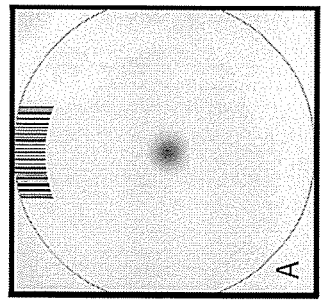

FIG. 3 shows the results of illuminating applanation cornea-cap interface 34 of a pig using near infrared light. However, similar results are obtained using visible illumination light. A portion of the illumination light reaching cornea-cap interface 34 will be reflected back and be visible by retina-cornea image sensor 50. Indicia 70 are also shown. The reflection is the result of the differences in the index of refraction between the applanation cap and either ambient air or aqueous from the subject's tear film. When the applanation cap is in contact with the cornea, the contacted portion of the illumination light is transmitted through the applanation cap and will appear darker when viewed by the image sensor as shown as applanation area 74. Thus, the darker circle will grow in size as greater force is exerted on the cornea. In this example, the pressure in the pig's eye was initially set at 10 mmHg with a monometer. Incremental increases in force on the ocular globe will result in incremental increases in intraocular pressure above the initially set 10 mmHg. Maximum applanation area 72 is shown as a circular line as a reference to the user. In this example and upon contact of the applanator with the pig's eye, the results are as follows:

|  | Diameter/Area | Force | Measured pressure |
|---|---|---|---|
| FIG. 3A | 0.91 mm/0.007 cm$^2$ | 0.50 gF | — |
| FIG. 3B | 3.54 mm/0.098 cm$^2$ | 1.06 gF | 10.8 mmHg |
| FIG. 3C | 6.31 mm/0.313 cm$^2$ | 3.55 gF | 11.3 mmHg |

Figure 4:
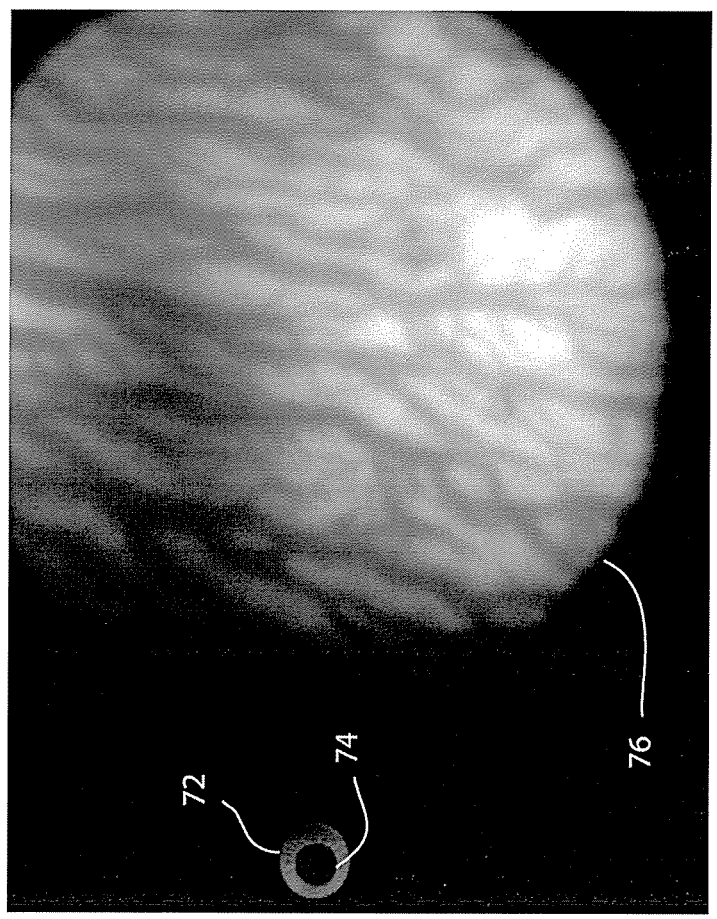
FIG. 4 depicts an image from a single retina-cornea image sensor system according to the present disclosure.

FIG. 4 shows an image taken by a single retina-cornea image sensor system similar to that shown in FIG. 2. The larger retinal fundus 76 and smaller corneal applanation area 74 were taken of a rabbit. In the image shown, a 1.3 megapixel (1280H×1024V) CMOS sensor was used. However, the selection of sensor depends upon the design of the optical train, the illumination, the desired field of view, the frame rate, etc. A person of skill in the art will select appropriate optical and opto-mechanical elements to meet the desired system specifications. A large field of view and high-resolution image is beneficial for retinal imaging. The large retinal field of view allows for more rapid identification of the optic disk. Higher resolution also permits the ability to electronically select the area of interest and maintain sufficient resolution to observe vessel collapse. In this illustrative example, satisfactory retinal images were obtained using approximately 1024×1024 px field. In contrast, determination of corneal applanation size was effectively obtained using a 256×256 px field.

FIG. 5 depicts an exemplary dual sensor system 150 according to the present invention. This system provides retinal illumination and imaging, corneal illumination and imaging, and a fixation point as described below. For convenience, the retinal illumination aspect of the system 150 is described first and is highlighted in FIG. 6. While reference to retinal illumination is used herein, it should be understood that reference to the 'retina' or 'retinal' is to include blood vessels leading to and from the retina and more particularly the central retinal artery and vein.

Figure 6:
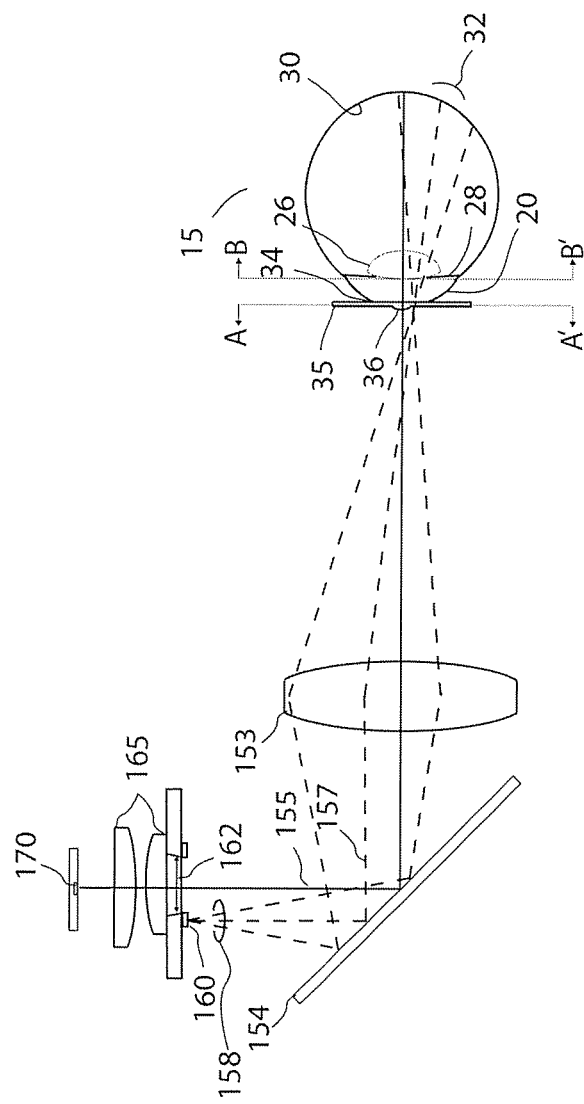
FIG. 6 depicts an exemplary retinal imaging and illumination system shown in FIG. 5 and according to the present invention.
Figure 7:
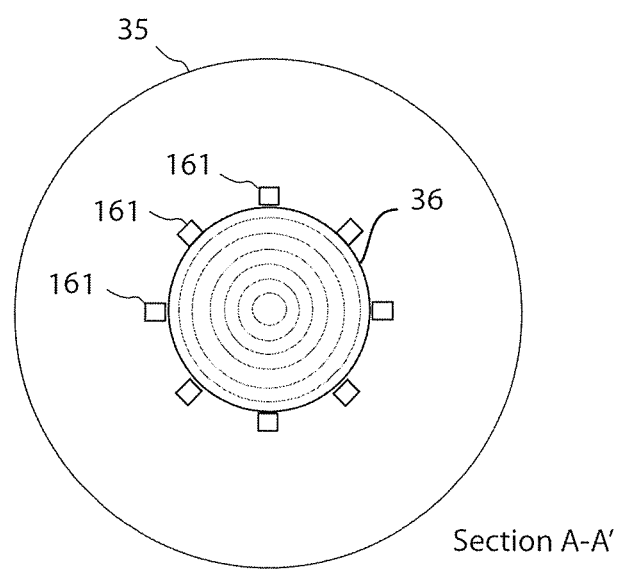
FIG. 7 depicts a first exemplary cross-section view of an illumination pattern of the applanation cap in accordance with the present invention.
Figure 8:
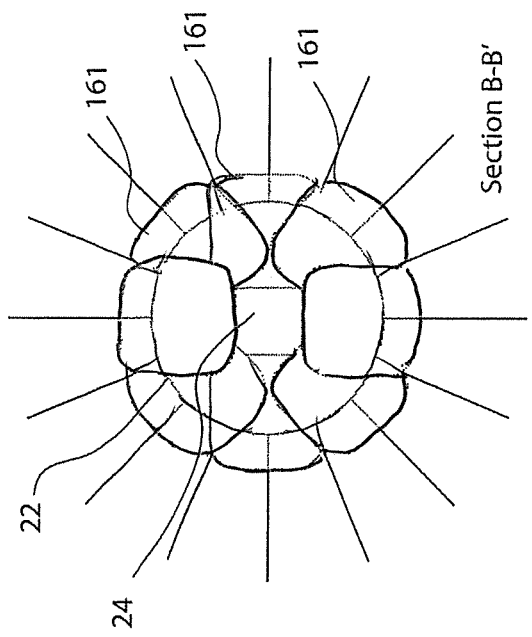
FIG. 8 depicts a second exemplary cross-section view of an illumination pattern of the applanation cap in accordance with the present invention.

Retinal illumination light source 160 may be a ring of light sources including for example light emitting diodes (LED's) that emit light along path 157 (one LED illustrated for simplicity of the explanation and shown as a dotted line). Retinal illumination light 158 is reflected by dichroic beam splitter 154, passes through and is focused by objective lens 153 and is incident on applanation cap 35. As shown in FIG. 6 and in cross-section A-A' in FIG. 7, retinal illumination light 158 is focused and forms a circular illumination pattern 161 on applanation cap 35 peripheral to convex shaped applanation cap lens 36. Cap lens 36 serves to compensate for the refractive power of the cornea lost due to applanating (flattening) cornea 20. Retinal illumination light 158 diverges and forms illumination pattern 161 as it passes through pupil 24. The iris is shown, but not labeled. Section B-B' in FIG. 6 shown in cross section in FIG. 8, illustrates the relative size of retinal illumination pattern 161 in the plane of iris 28. A constricted iris may vignette a portion of the light, yet provide sufficient illumination to image retina 30 on retina image sensor 170 through an un-dilated, 2.4 mm pupil. However, adequate illumination through smaller diameter pupils is also possible. In this embodiment and as shown in FIGS. 6, 7 and 8, illuminating the retina through illumination path 157 peripheral to cap lens 36 and central pupil 24, obviates the illumination path being coaxial with retina imaging path 155 that is positioned along the central optical axis of globe 15. The sclera is shown but not labeled. However, in this configuration, both illumination and imaging paths share objective lens 153. As a result this configuration minimizes or eliminates illumination light reflected back to retina image sensor 170 from objective lens 153, applanation cap 35, cornea 20 and ocular lens 26. Various image stops or apertures such as retinal image aperture 162 may be added to further reduce stray light from entering retina image sensor 170. One or more focusing lenses 165 may be present to adjust retinal or other lighting. Corenal focusing lens 210 may also be present.

Figure 11:
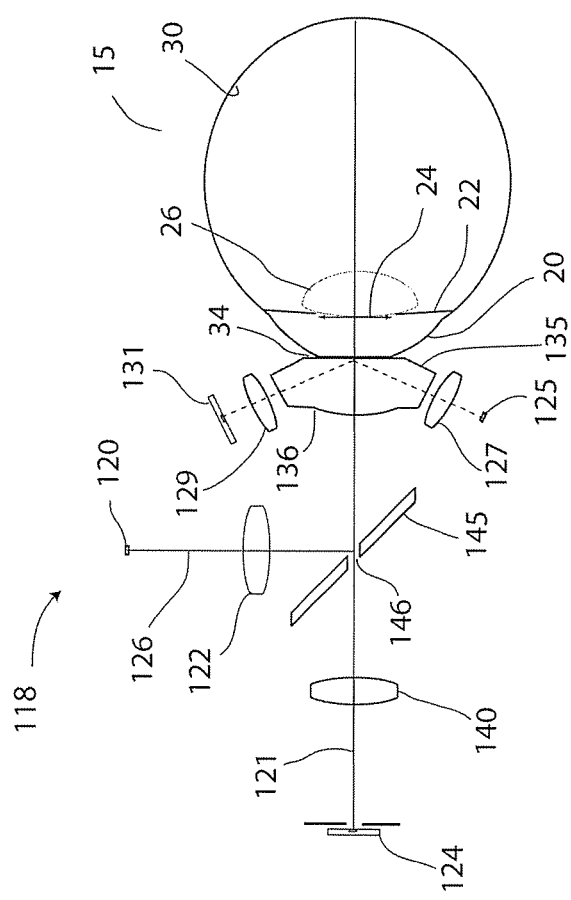
FIG. 11 depicts a second exemplary dual image sensor system according to the present invention.

There are numerous techniques known in the art to illuminate the retina with light entering the eye through the central pupil. For example a total reflecting mirror with an aperture positioned along the illumination axis may be used in place of dichroic beam splitter 154. This is shown in FIG. 11 as aperture 146 in aperture mirror 145. In this configuration a ring of illumination light is created thereby minimizing reflections back to the retinal image sensor.

Figure 9A:
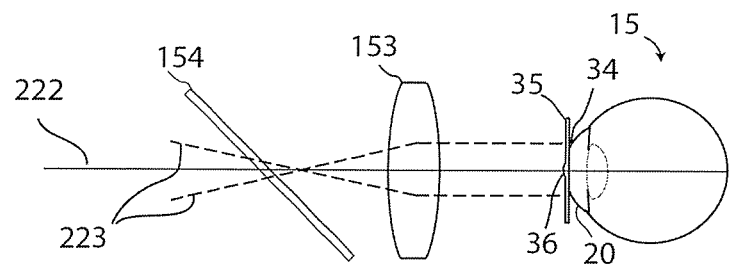
FIG. 9A depicts a portion of a corneal imaging and illumination system shown in FIG. 5 and according to the present invention.

FIG. 5 shows a scheme for illuminating and imaging cornea-cap interface 34 along the central axis of the globe and sharing objective lens 153. Cornea illumination source 220 light passes through dichroic beam splitters 205 and 235. Field lens 200 focuses illumination source light to an apex in proximity to dichroic beam splitter 154. Illumination light is then collimated by objective lens 153 onto applanation cap 35 as better shown in FIG. 9A illustrating cornea illumination rays 223. The collimated illumination light is reflected by applanation cap 35 back to dichroic beam splitter 205 and corneal focusing lens 201, aperture 212 onto corneal image sensor 215. Retinal imagine axis 155 is shown. Cornea illumination path 222 is shown, as well. Fixation light source 230 is also shown.

As used in one illustrative corneal applanation imaging system, applanation cap 35 is flat plane of PMMA with a very small, 2 mm in diameter cap lens 36. The incident illumination light will be normal to flat plane of applanation cap 35. Therefore, the reflectance, R, from each surface, proximal and distal, with a refractive index $n_0$ of air=1 and a refractive index $n_1$ of PMMA=1.492, is given by $$R_P = \left[\frac{(n_0 - n_1)}{(n_0 + n_1)}\right]^2.$$

Therefore, 3.9% of the incident light is reflected from the proximal surface of the cap and 3.9% from the distal surface where the cap is not applanating the cornea. When the distal surface of applanation cap 35 is contacting cornea 20 having an index of refraction $n_C$=1.33, the distal surface will reflect $$R_D = \left[\frac{(n_1 - n_C)}{(n_1 + n_C)}\right]^2 = 0.3\%.$$

Figure 9B:
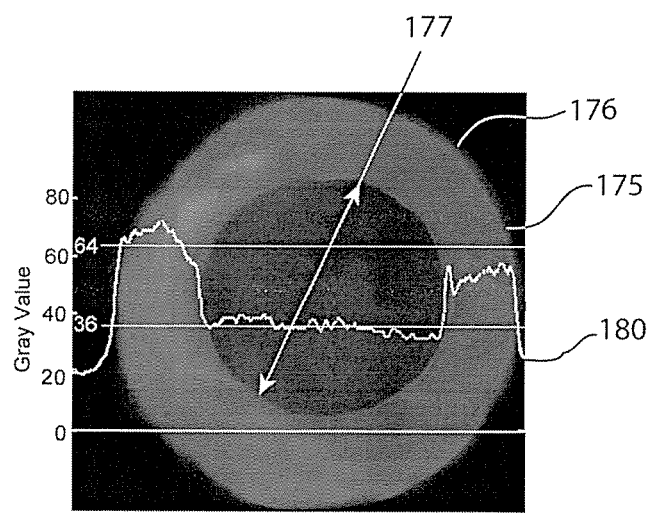
FIG. 9B depicts a corneal applanation image from the system shown in FIG. 5 and according to the present invention.

As a result, the applanated area of cap 35 cornea will reflect 3.9%+0.3% or 4.2% of the incident light and the non-applanated area will reflect 3.9%+3.9% or 7.8%. Thus cornea image sensor 215 will show an almost 2:1 contrast ratio of applanated to non-applanated areas on contact. FIG. 9B illustrates an applanated area using collimated light. In this example, darker applanated area 177 has a grey value of approximately 36 and is surrounded by lighter maximum applanation area 176 having a grey value of approximately 64. 175 represents an applanation image.

Figure 10:
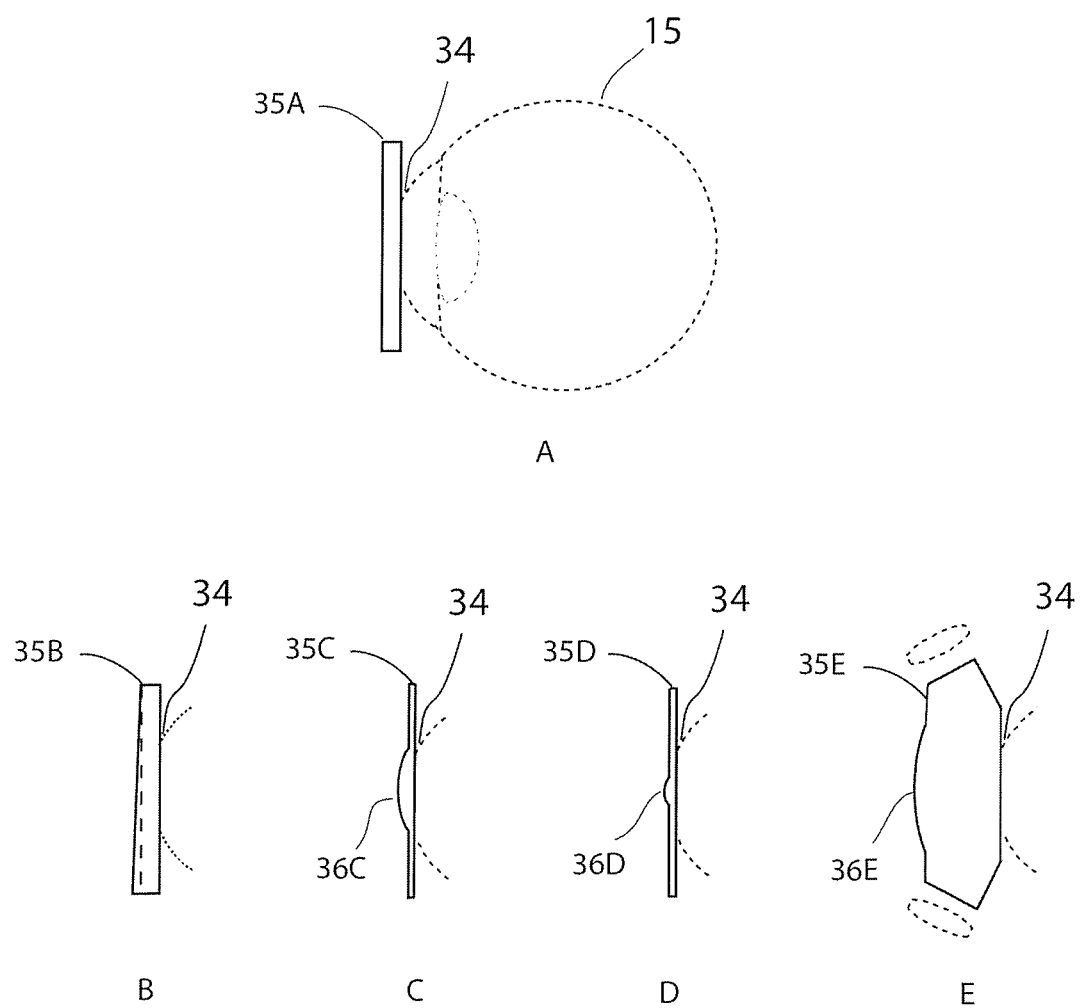
FIG. 10 depicts exemplary applanation caps in accordance with the present invention.

FIG. 10 depicts various configurations of applanation cap 34 that are within the scope of the present disclosure. Alterations in the anterior refractive surface of an applanation cap provide a host of optical design options. For example, FIG. 9A shows the cornea of globe 15 being applanated by planoplano applanation cap 35A. As shown, the function of the cap is solely to applanate the cornea. Upon applanation, the pressure in the eye will be elevated and there will be complete loss of the refractive power by the cornea. Conventional fundus cameras are dependent on corneal refractive power to view the retina. As a result plano-plano applanation cap 35A obviates use of such camera to view the retina. Further, such cameras have no means to simultaneously view the cornea.

The configuration of the system shown in FIG. 5 and highlighted in FIGS. 6 and 9A overcome the limitations of a conventional fundus camera. Such a configuration will permit viewing the retina along the optical axis of the eye centered on the fovea. The optic disc, from which the optic nerve and central retinal artery and vein enter the retina, is located approximately 3 mm nasal and 1 mm superior to the fovea.

FIG. 10B illustrates applanation cap 35B, which is similar to applanation cap 35A but has a prismatic element permitting a shift in the image of the retina. This may permit viewing the retina with the system aligned along the optical axis of the eye, but centered on the optic disc. FIGS. 10C, D and E show applanation caps 35C, 35D and 35E with applanation cap lenses 36C, 36D and 36E respectively. The cap lenses have suitably positive (convex) surfaces on the anterior surface to replace some or all of the optical power of the cornea lost during applanation. The configuration and size of the applanation cap and cap lens is chosen in concert with the rest of optical module. Three representative optical module configurations are illustrated herein and are not to be viewed as limiting. Other optical module configurations and caps can be designed within the teaching and spirit of the invention by one of skill in the art.

As stated, the applanation cap may be of any material compatible with the cornea such as polycarbonate, polymethyl methacrylate (PMMA) or even glass. The applanation cap diameter can range from about under 4 mm to over 15 mm.

The parameter that determines the applanation cap diameter is the degree of globe applanation. For applanating an adult cornea, a convenient size is 10 mm. This diameter does not include the area for handling or conveniently mounting the applanation cap.

In another embodiment of the disclosed invention, a conventional optical configuration for viewing the retinal fundus is used that does not share the optical path for viewing applanation area of the globe. While corneal applanation techniques for collapsing the retinal vessels and determination of intraocular pressure is one preferred embodiment, it is understood that applanation may be accomplished by applanation of the sclera as well. However, any means of applanation can be used that can be configured to permit a view of the blood vessels within the optic disk and determine intraocular pressure. Suitable methods may include but not be limited to corneal applanation tonometry, pneumotonometry (also referred to a 'air-puff tonometry"), electronic indentation tonometry, transpalpebral (through the eyelid) tonometry, and the like.

FIG. 11 depicts an exemplary embodiment based on use of a retinal fundus viewing system that does not share an optical path with the path used for measuring intraocular pressure. Several retinal imaging and illumination configurations are well known in the art, one of which is shown in this embodiment. Applanation cap 135 is positioned to applanate the cornea and form cornea-cap interface 34. Cornea-cap interface 34 is preferably flat but may be shaped to accommodate placement on the cornea and modifications in the intraocular pressure measuring scheme. As shown in this figure, retinal illumination source 120 emits light along retina illumination path 126, which light is directed by lens or lenses 122 and is reflected by apertured mirror 145. Apertured mirror 145 has aperture 146 positioned along retinal imaging path 121. Aperture 146 permits an un-obscured optical path for imaging the retina. Further, it does not reflect retinal illumination along the central axis of imaging path 121, and as a result it reduces or eliminates light reflected back toward retinal imaging sensor 124. Retinal illumination is transmitted through and focused by applanation cap lens 136, passes through pupil 24 and suitably reflects from one or more intraocular blood vessels of retina 30. Cap lens 136 is a convex surface on proximal side of applanation cap 135 designed to replace some or all of the refractive power of the cornea during applanation.

Light reflected from retina 30 passes through pupil 24 and applanation cap 135 and is focused by cap lens 136 to an apex at or near aperture 146. Reflected light is then focused by retinal focusing lens or lenses 140 onto retina image sensor 124.

An exemplary cornea applanation measurement scheme is also shown in FIG. 11. Corneal illumination source 125 projects illumination light by way of corneal illumination lens 127 to cornea-cap interface 34. As described herein and as a result of changes in the index of refraction at the corneacap interface, the pattern of light at cornea-cap interface 34 changes as a function of the force applied and resulting degree of applanation of the cornea by applanation cap 135. The pattern of reflection and resulting intensity of illumination light from cornea-cap interface 34 is focused by cornea imaging lens 129 onto cornea image sensor 131. Thus, ICP measuring system 118 is suitable to simultaneously image the degree of applanation by applanation cap 135 on the cornea and, image blood vessels in the optic disk of the retina. Imaging axis 121 is also shown. An imaging aperture (not labeled) may be present in communication with the image sensor 124.

The disclosed systems are not limited to the imaging or illumination arrangements shown in the figures. In one of several variations, light from the illumination source 120 may be one or more LED's configured to pass through an axicon lens (not shown) forming a ring of light directed by a dichroic beam splitter to applanation cap 135.

The conventional lenses in the ICP measurement system have been discussed herein. However, such lenses can be replaced using similarly functioning optical elements including diffractive lenses, holographic optical elements, graded index lenses and hybrid optical elements.

The present invention has been shown and described with reference to exemplary drawings and not drawn to scale, it will be understood by one of skill in the art that various changes in detail may be affected without departing from the scope or spirit of the invention as defined by the claims.

What is claimed:

1. A system for measuring intracranial pressure in a subject, comprising:
    an applanator configured to controllably at least partially applanate a portion of a subject's ocular globe;
    an ophthalmic component configured to engage with the applanator;
    a first image collector configured to collect light reflected from an intraocular blood vessel of the subject;
    an illumination train configured to direct light through the ophthalmic component to the intraocular blood vessel of the subject and to direct light reflected from the intraocular blood vessel to the first image collector,
    wherein the illumination train is further configured to direct illumination reflected from an interface between the ophthalmic component and an applanated region of the subject's ocular globe, wherein a portion of the illumination passes through a contacted portion of the interface and a portion of the illumination reflects off the interface; and
    a processor configured to estimate an intracranial pressure of the subject based on illumination reflected from the at least partially applanated portion of the subject's ocular globe and illumination reflected from the intraocular blood vessel of the subject.

2. The system of claim 1, wherein the ophthalmic component bears one or more indicia and the system is capable of self-configuring at least one of the applanator, the image collector, or the illumination train in response to one or more indicia present on the ophthalmic component.

3. The system of claim 1, wherein the system is configured to, during operation, concurrently applanate at least a portion of the subject's ocular globe and collect, on the first image collector, light reflected from the intraocular blood vessel of the subject.

4. The system of claim 3, wherein the system is further configured to collect, on the first image collector, light reflected from an interface between the ophthalmic component and the ocular globe of the subject.

5. The system of claim 3, wherein the system is further configured to collect, on a second image collector, light reflected from an interface between the ophthalmic component and the ocular globe of the subject.

6. The system of claim 1, thither comprising a Doppler instrument configured so as to collect ultrasound data from a periocular blood vessel of the subject.

7. The system of claim 1, wherein the system is configured to estimate an intraocular pressure based on one or more of a three that least partially applanates the portion of a subject's ocular globe, an area of the at least partially applanated portion of the subject's ocular globe, or both.

8. The system of claim 1, wherein the system is configured to assess the degree, if any, of papilledema present in the subject.

9. The system of claim 1, wherein the system is configured to compare the estimated intracranial pressure with an estimated intraocular pressure of the subject.

10. The system of claim 1, wherein the system is configured to, during operation, record retinal fundus images, score features of the optic disc using image processing algorithms, or both.

11. The system of claim 10, wherein the system is configured to compare retinal fundus images to a database of images so as to grade papilledema, if present, according the Frisén Scale.

12. A system, comprising:
    an applanator configured to controllably applanate at least a portion of the ocular globe of a subject,
    a first image collector configured to collect light reflected from an intraocular blood vessel of the subject; and
    an illumination train configured to direct light through an ophthalmic component to the intraocular blood vessel of the subject and to direct light reflected from the intraocular blood vessel to the image collector,
    the system configured to, during operation, record retinal fundus images, and
    the system configured to compare retinal fundus images to a database of images so as to grade papilledema, if present, according the Modified Frisén Scale.

* * * * *